(12) United States Patent
Huang et al.

(10) Patent No.: US 6,287,778 B1
(45) Date of Patent: Sep. 11, 2001

(54) ALLELE DETECTION USING PRIMER EXTENSION WITH SEQUENCE-CODED IDENTITY TAGS

(75) Inventors: Xiaohua Huang, Mountain View; Tom Ryder, Los Gatos; Paul Kaplan, Campbell, all of CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 09/420,805

(22) Filed: Oct. 19, 1999

(51) Int. Cl.$^7$ ....................................................... C12Q 1/68
(52) U.S. Cl. .................. 435/6; 435/5; 435/91.1; 435/91.2; 435/69.7; 536/26.1; 536/26.12; 536/23.1; 536/24.33
(58) Field of Search ................. 435/6, 5, 91.1, 435/91.2, 23.1; 536/26.12, 23.1, 24.33, 26.1

(56) References Cited

U.S. PATENT DOCUMENTS 5,455,169 * 10/1995 Mullan ............................. 435/240.2
5,700,637 12/1997 Southern .
6,004,744 * 12/1999 Goelet et al. ............................. 435/5
6,013,439 * 1/2000 Lishanski et al. ........................ 435/6

FOREIGN PATENT DOCUMENTS

89/10977   11/1989  (WO) .

* cited by examiner

Primary Examiner—W. Gary Jones
Assistant Examiner—Janell E. Taylor
(74) Attorney, Agent, or Firm—Banner & Witcoff, Ltd.

(57) ABSTRACT

A method for determining the genotype of one or more individuals at a polymorphic locus employs amplification of a region of DNA, labeling of allele-specific extension primers containing tags, and hybridization of the products to an array of probes. The genotype is identified from the pattern of hybridization. The method can also be used to determine the frequency of different alleles in a population.

72 Claims, 2 Drawing Sheets

ALLELE DETECTION USING PRIMER EXTENSION WITH SEQUENCE-CODED IDENTITY TAGS

FIELD OF THE INVENTION

The invention is related to the area of genome analysis. In particular it is related to the field of identification of bases at particular locations in a nucleic acid molecule.

BACKGROUND OF THE INVENTION

Obtaining genotype information on thousands of polymorphisms in a highly parallel fashion is becoming an increasingly important task in mapping disease loci, in identifying quantitative trait loci, in diagnosing tumor loss of heterozygosity, and in performing association studies. A currently available method for simultaneously evaluating large numbers of genetic polymorphisms involves hybridization to allele-specific probes on high density oligonucleotide arrays. In order to practice that method, redundant sets of hybridization probes, typically twenty or more, are used to score each allelic marker. A high degree of redundancy is required to reduce noise and achieve an acceptable level of accuracy. Even this level of redundancy is insufficient to unambiguously score heterozygotes or to quantitatively determine allele frequency in a population.

The technique of allele-specific polymerase chain reaction (ASPCR) can be applied to allele identification and quantitative analysis of allele frequency. However, this technique suffers from cross reactivity between amplified products when hybridizing to probes which differ by only a single nucleotide base. A partial solution to the cross-reactivity problem has been achieved by the addition of sequence tags to the ASPCR primers. The incorporation of tags in ASPCR primers can itself interfere with the identification of the amplification products because unreacted primers or partially extended products can compete with full products for hybridization to the probes. Thus, there is a further need in the art for methods and materials which permit the accurate determination of polymorphic loci without interference from incompletely reacted products.

SUMMARY OF THE INVENTION

It is an object of the invention to provide methods and compositions for the identification of nucleotides at a polymorphic locus in a nucleic acid sequence. This and other objects of the invention are provided by one or more of the embodiments described below.

In one embodiment of the invention, a method is provided to aid in detecting a selected allele of a gene in a sample. A region of single or double stranded DNA in the sample is amplified using one or a pair of amplification primers to form an amplified DNA product. The region comprises a polymorphic locus of the selected allele of the gene. An extension primer is labeled in the presence of the amplified DNA product, which serves as the template for the labeling reaction. The extension primer comprises a 3' portion which is complementary to the amplified DNA product and a 5' portion which is not complementary to the amplified DNA product. The extension primer also terminates in a 3' nucleotide at the polymorphic locus of the selected allele. At least one labeled nucleotide is coupled to the 3' terminal nucleotide of the extension primer to form a labeled extension primer. The labeled extension primer is hybridized to a probe on a solid support. All or a portion of the probe is complementary to the 5' portion of the extension primer.

Another embodiment of the invention provides another method to aid in detecting a selected allele of a gene in a sample. A region of single or double stranded DNA in the sample is specifically amplified using one or a pair of amplification primers to form an amplified DNA product. The region comprises a polymorphic locus of the selected allele of the gene. An amplification primer terminates in a 3' nucleotide at the polymorphic locus of the selected allele. An extension primer is labeled in the presence of the amplified DNA product, which serves as the template for the labeling reaction. The extension primer comprises a 3' portion which is complementary to the amplified DNA product and a 5' portion which is not complementary to the amplified DNA product. The extension primer also terminates in a 3' nucleotide at the polymorphic locus of the selected allele. At least one labeled nucleotide is coupled to the 3' terminal nucleotide of the extension primer to form a labeled extension primer. The labeled extension primer is hybridized to a probe on a solid support. All or a portion of the probe is complementary to the 5' portion of the extension primer.

Yet another embodiment of the invention is a kit which comprises in a single container a set of primers for use in detecting a selected allele of a gene. The set of primers includes a pair of primers which amplify a region of the gene comprising a polymorphic locus and an extension primer which terminates in a 3' nucleotide which is the polymorphic locus of the selected allele. A 3' portion of the extension primer is complementary to the selected allele, and a 5' portion of the extension primer is complementary to all or a portion of a probe on a solid support but not complementary to the amplified region of the gene.

Still another embodiment of the invention is a kit which comprises in a single container a set of primers for use in detecting an allele. The set of primers includes a pair of primers which specifically amplify a selected allele and an extension primer. The pair of primers comprises a first and a second primer. The first and second primers are complementary to opposite strands of a DNA target. The first primer and the extension primer each terminate in a 3' nucleotide which is a polymorphic locus of the selected allele. A 3' portion of the extension primer is complementary to the selected allele, and a 5' portion of the extension primer is complementary to all or a portion of a probe on a solid support but not complementary to the amplified region of the DNA target.

Still another embodiment of the invention provides another method to aid in detecting a selected allele of a gene in a sample. A region of single or double stranded DNA in the sample comprises a polymorphic locus of the selected allele of the gene. An extension primer is labeled in the presence of the region of DNA which serves as the template for the labeling reaction. The extension primer comprises a 3' portion which is complementary to the region of DNA and a 5' portion which is not complementary to the region of DNA. The extension primer also terminates in a 3' nucleotide at the polymorphic locus of the selected allele. At least one labeled nucleotide is coupled to the 3' terminal nucleotide of the extension primer to form a labeled extension primer. The labeled extension primer is hybridized to a probe on a solid support. All or a portion of the probe is complementary to the 5' portion of the extension primer.

The invention thus provides the art with sensitive and specific methods and compositions for identification of polymorphic nucleotides in a DNA sample which may be from one or more individuals.

DETAILED DESCRIPTION OF THE INVENTION

Figure 1:
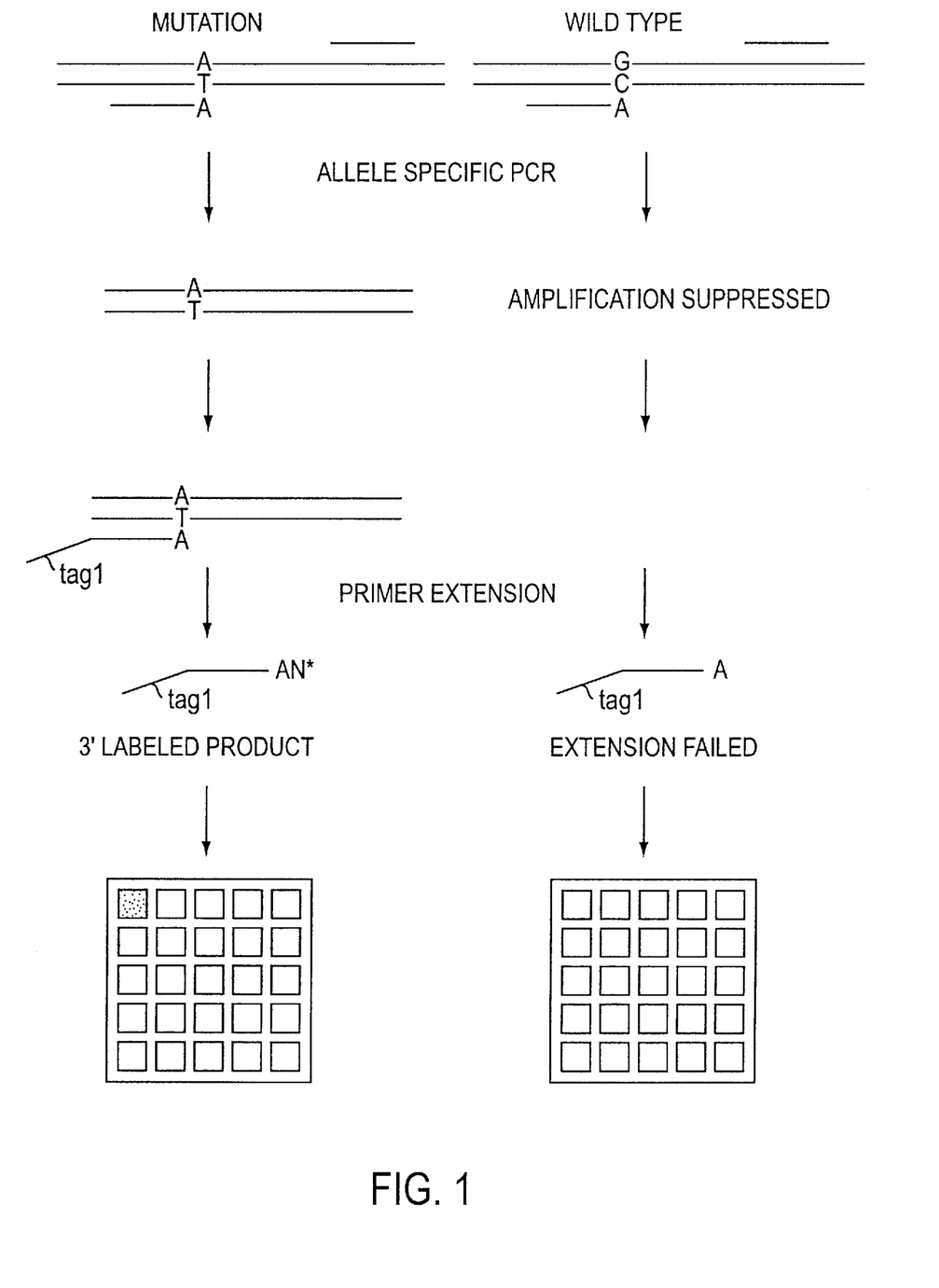
FIG. 1 illustrates a method of determining nucleotides at a polymorphic locus. The first step shows the use of allele specific polymerase chain reaction (ASPCR) primers to amplify only those regions of the double stranded DNA sample which contain a specific nucleotide at a polymorphic locus. In the second step, the amplification product serves as the template for a primer extension reaction. The primer contains a tag at its 5' end and terminates in a 3' nucleotide at the polymorphic locus. The final step shown is the hybridization of the labeled extension product to a solid support to which a probe is attached that is complementary to the tag at the 5' end of the extension primer.
Figure 2:
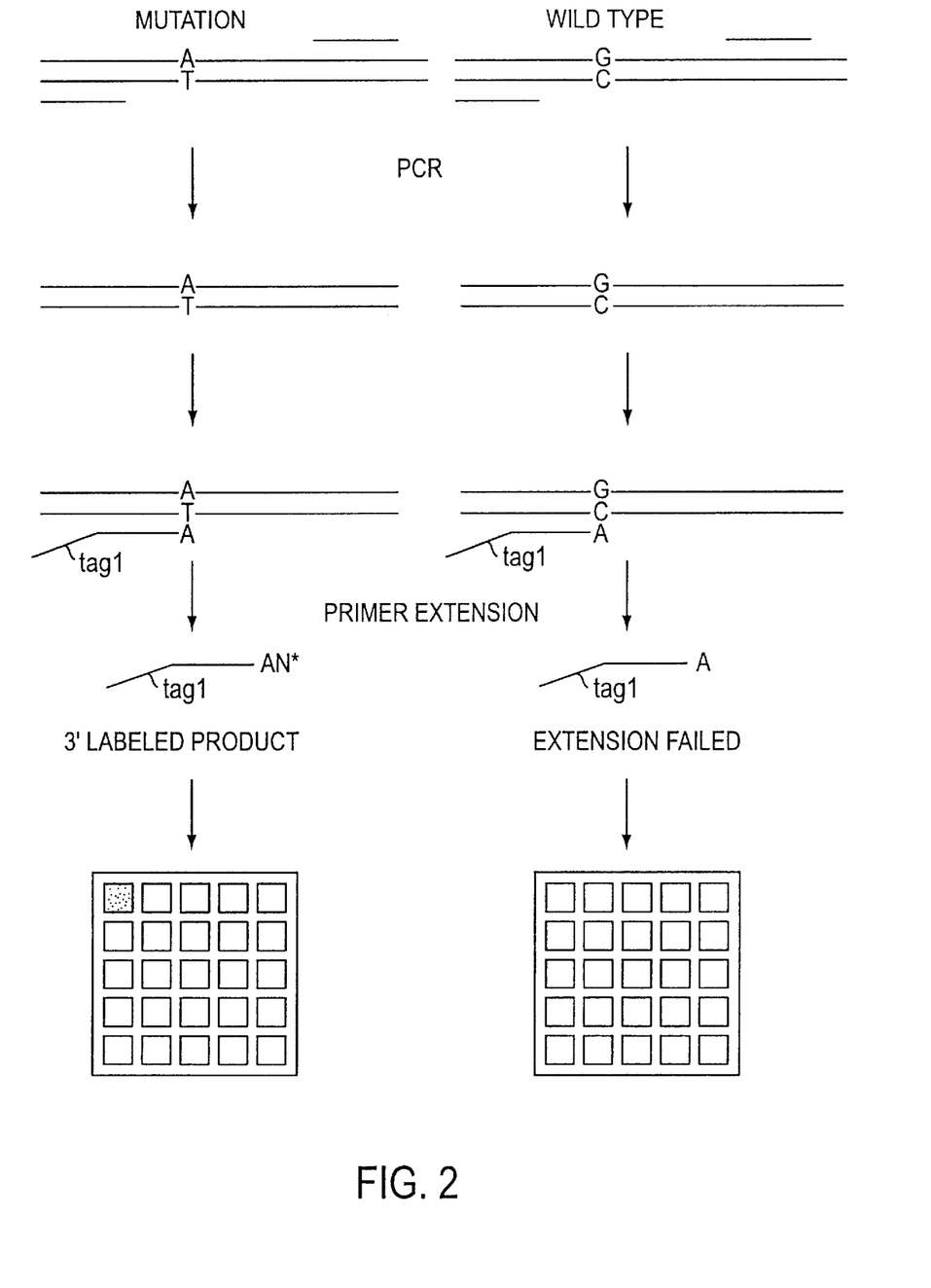
FIG. 2 illustrates another method of determining nucleotides at a polymorphic locus. The first step involves the use of polymerase chain reaction (without allele specificity) to amplify a region of the double stranded DNA sample which contains a specific polymorphic locus. In the second step, the amplification product serves as the template for a primer extension reaction. The primer contains a tag at its 5' end and terminates in a 3' nucleotide at the polymorphic locus. The final step shown is the hybridization of the labeled extension product to a solid support to which a probe is attached that is complementary to the tag at the 5' end of the extension primer.

It is a discovery of the present inventors that determination of a base at a polymorphic locus can be accomplished with great specificity and sensitivity by incorporating unique tags into allele-specific nucleic acids and hybridizing them to tag-specific probes on a solid support. A nucleic acid sample is optionally amplified in a manner which is either allele specific or not allele specific. The amplification products can serve as the template for a primer extension reaction using uniquely tagged, allele-specific primers. A labeled extension product is formed for each primer only if the respective allele was present in the original nucleic acid sample. Extension products corresponding to different alleles are linked to different tags. Each tag comprises a sequence that is complementary to all or part of a corresponding probe at a known location on a detection array. The use of a unique tag for each allele eliminates the problem of cross-hybridization which arises with other methods. Furthermore, the use of tags eliminates interference from unreacted amplification primers and partially extended products. Such problems can prevent unambiguous determination of polymorphic alleles.

A diploid organism, for example a human, possesses two copies of each type of autosomal gene in its somatic cells. A population of organisms may contain several variants of a gene, known as alleles. A "polymorphic locus" is a location within a genome which exhibits genetic polymorphism, i.e., a location where one or more nucleotides may vary in the genomes of different individuals. Such variations can arise due to inherited mutations, or they can arise as de novo mutations in an individual organism. An "allelic form" is a specific variant of a gene embodied in a nucleic acid molecule, e.g., genomic DNA, an RNA transcript, a CDNA, a synthetic nucleic acid bearing the sequence of the variant, or a protein molecule encoded by the variant. Different allelic forms differ from one another by single basepair substitutions (also called single nucleotide polymorphisms or SNPs), or they can differ by two or more bases. Different allelic forms can also arise by insertion or deletion mutations. Any known allelic form at a polymorphic locus can be identified and quantified with the methods described here.

Briefly, two steps can be employed to determine a polymorphic nucleotide: labeling and hybridizing. An optional amplification step can precede the labeling and can be either allele-specific or not allele-specific. Allele-specific amplification of a nucleic acid sample according to the present invention uses at least one allele-specific primer; the primer has an allele-specific 3' end. For amplification without allele specificity, the primers lack an allele-specific 3' end. The sample nucleic acid or amplification products are used as templates with an extension primer to add one or more nucleotides, preferably labeled, to the extension primers. Each extension primer contains a tag sequence which is complementary to all or part of a probe in an array on a solid support. Each extension primer also has an allele-specific 3' end. The labeled extension products are hybridized to probes on a solid support. An additional optional step involves the optical detection of fluorescently labeled, hybridized amplification products.

The genotype of an individual at a polymorphic locus can be determined from the hybridization. If the nucleic acid sample being tested is derived from a population or group of individual organisms, an allele frequency or the ratio of allelic forms in the population can be quantified. A plurality of polymorphic loci in a given nucleic acid sample can be simultaneously analyzed in a single reaction mixture using a plurality of pairs of primers and/or a plurality of extension primers. Alternatively, individually labeled extension primers can be mixed and hybridized on a single solid support.

A "tag" or "sequence tag" is a nucleotide sequence which is complementary or nearly complementary to the sequence of all or a portion of a probe in an array. A tag sequence need only be sufficiently complementary to its respective probe sequence to permit specific binding between them, without sufficient binding to other probes to confuse the assignment of tag to probe. However, it is preferred that each base of a tag sequence be complementary to each corresponding base of the respective probe sequence. Tags and probes need not be identical in length. The appropriate length for tags and probes is such that a tag and its respective probe hybridize with high affinity and high specificity. Important factors include, for example, length of the tag and probe sequences, the number and position of mismatching bases, if any, and the characteristics of the solution in which hybridization is carried out, especially its ionic strength and pH. Each probe and its corresponding tag share a complementary region that preferably lacks any mismatched bases and is at least 12, 14, 16, 18, 20, 22, 24, 26, 28, 30, 35, or 40 nucleotides in length.

The sequence tags are typically unrelated to the sequences of the polymorphic alleles which are being analyzed. The sequence tags are chosen for their favorable hybridization characteristics. The tags are typically selected so that they have similar hybridization characteristics to each other and minimal cross-hybridization to other tag sequences. Each sequence tag is attached to an extension primer for a particular allele, and serves as a label or address for that particular allele.

A generic solid support, corresponding to the pre-selected tag sequences can be fabricated and used to detect the presence, absence, or ratio of specific allelic forms in a test sample. See U.S. Pat. No. 5,800,992, application Ser. No. 08/626,285 filed Apr. 4, 1996, and EP application no. 97302313.8 which are expressly incorporated by reference herein.

The DNA in the sample analyzed can be of any source, including genomic, nuclear, cDNA, mitochondrial DNA, macronuclear DNA, and micronuclear DNA. The DNA can be isolated from one or more individuals. The DNA can be purified to contain only a certain subset of cellular DNA, if desired. Any type of amplification reaction can be used, including PCR, ligase chain reaction, transcription amplification, and self-sustained sequence replication. Thus, appropriate enzymes such as DNA polymerase or DNA ligase will be used as desired by the artisan.

Each amplification primer or pair of amplification primers amplifies a region of DNA containing a polymorphic locus. Pairs of primers can comprise a first primer and a second primer. The first and second primers can be complementary to opposite strands of the DNA region to be amplified. If the amplification step is to be allele specific, the first primer of the pair terminates in a 3' nucleotide which is complementary to a specific allelic form but not complementary to other allelic forms. If the amplification step is not to be allele specific, then the first primer terminates at its 3' end, 5' to the polymorphic locus.

In an alternative embodiment the amplification step can be omitted. Thus, if sufficient DNA is available, the primer extension reaction can be performed directly on sample DNA. In another alternative embodiment, amplification of the entire population of sample DNA can be performed using random primers.

The amplified DNA product or sample nucleic acid is labeled using a template-dependent primer extension reaction prior to its hybridization to a probe on a solid support. Any such reactions known in the art can be used, including but not limited to a single base extension reaction using a DNA polymerase. The extension primer is allele-specific and terminates at its 3' end in the polymorphic locus. The extension primer contains a portion at its 3' end which is complementary to the amplified DNA product. The extension primer also contains at its 5' end a portion which comprises a tag. The nucleotide sequence of the tag is complementary to all or a portion of a probe on a solid support. The tag and corresponding probe sequences are specifically chosen-so as not to share a complementary region with the region of DNA which is amplified; this prevents cross-hybridization of other labeled amplified products with the probe. Preferably, no probe on the solid support shares a region of complementary sequence with an amplified DNA region greater than 2, 3, 4, 5, 6, 8, or 10 consecutive bases.

The labeled extension product can be hybridized to one or more probes which are immobilized to known locations on a solid support, e.g., in an array, microarray, high density array, beads, or microtiter dish. Each probe is of opposite complementarity as a corresponding tag on an extension primer. The quantities of the label at known locations on the solid support can be compared, and the genotype can be determined for an individual or the allele frequency can be determined for a population from whom the DNA in the sample was obtained.

The reactions of the present invention can be performed in a single or multiplex format. For example, the amplification step can be performed using up to 20, 30, 40, 50, 75, 100, 150, 200, 250, or 300 different primer pairs to amplify a corresponding number of polymorphic markers. These can be pooled for the primer extension reaction, if desired. Pooling for the hybridization step is desirable so that thousands of hybridizations can be performed simultaneously. The results can be expressed qualitatively (presence or absence of given nucleotides at each polymorphic locus in a DNA sample) or quantitatively (ratio of different nucleotides at each polymorphic locus).

The ability to perform the method of the present invention in a multiplex manner for a number of different polymorphic loci simultaneously is due to the sequence tags which are present on the extension primers at their 5' ends. The sequence tags permit the operator to ultimately sort the products of multiplex amplification and multiplex primer extension to different locations on an array. Each sequence tag on an extension primer is used for a single allele.

Sets of primers according to the present invention comprise an amplification pair and one or more extension primers. These may be packaged in a single container, preferably a divided container or package. The pair of primers amplifies a region of double stranded DNA which comprises a polymorphic locus. The extension primer has two portions, a 3' portion which is complementary to a portion of the region of double stranded DNA which contains the polymorphic locus and a 5' portion which is not complementary to the region of double stranded DNA. The 5' region is the tag sequence which is complementary to the tag array which is used to sort and analyze the products of the primer extension reaction. The 3' end of the extension primer terminates at the polymorphic locus.

So long as the components are physically attached to each other or in a single package they form a kit. Such kits can additionally include a solid support comprising at least two probes, where each probe contains a different tag. Instructions for use according to the disclosed method, enzymes for amplification, buffers and control samples can be included as components in the kit.

Advantages of the disclosed method include that just one generic tag solid support can be used to genotype any genetic marker, i.e., no specific customized solid support is needed. In addition, the pre-selected probe sequences synthesized on the solid support guarantee good hybridization results between the probe and the tag, with little interference from cross-hybridization by closely related alletic sequences.

Providing a Nucleic Acid Sample

The terms "nucleic acid" or "nucleic acid molecule" refer to a deoxyribonucleotide or ribonucleotide polymer in either single- or double-stranded form, and unless otherwise limited, would encompass analogs of a natural nucleotide that can function in a similar manner as naturally occurring nucleotide. Suitable nucleic acid samples can contain polymorphic loci of interest. Suitable nucleic acid samples can also contain nucleic acids derived from a polymorphic locus of interest. As used herein, a nucleic acid derived from a polymorphic locus refers to a nucleic acid for whose synthesis the genomic DNA containing the polymorphic locus or a subsequence thereof has ultimately served as a template. Thus, a DNA amplified from genomic DNA, an RNA transcribed from the amplified DNA, an mRNA transcribed from the genomic DNA, or a cDNA reverse transcribed from the MRNA, etc., are all derived from the polymorphic locus, and detection of such derived products is indicative of the presence and/or abundance of the original polymorphic locus in a sample. Thus, suitable samples include, but are not limited to, isolated genomic DNA containing the gene or genes containing the polymorphic locus, an RNA transcript derived from the isolated genomic DNA, CDNA reverse transcribed from the transcript, CRNA transcribed from the cDNA, DNA amplified from the genes, RNA transcribed from amplified DNA, and the like. If the sample is a non-DNA sample, it can be converted to double stranded DNA prior to amplification per the invention, for example using reverse transcriptase and/or DNA polymerase. The sample can be derived from a single individual organism, e.g., human, animal, plant, or microbial. The sample can alternatively be derived from two or more organisms, in which case the determination will reveal information about allelic frequency within the population from which the nucleic acid sample was derived.

The nucleic acid sample can be a homogenate of cells or tissues or other biological samples. Preferably, the nucleic acid sample is a total DNA preparation of a biological sample. More preferably in some embodiments, the nucleic acid sample is the total genomic DNA isolated from a biological sample. The nucleic acid sample can be the total mRNA isolated from a biological sample. Those of skill in the art will appreciate that the total mRNA prepared with most methods includes not only the mature mRNA, but also the RNA processing intermediates and nascent pre-mRNA transcripts. For example, total mRNA purified with a poly (dT) column contains RNA molecules with poly (A) tails. Those polyA$^+$ RNA molecules could be mature mRNA, RNA processing intermediates, nascent transcripts or degradation intermediates.

Biological samples can be of any biological tissue or fluid or cells from any organism. Frequently the sample will be a "clinical sample," which is a sample derived from a patient. Clinical samples provide a rich source of information regarding the various alleles of a gene and their relation to disease. Some embodiments of the invention can be employed to detect mutations and to identify the phenotype of mutations. Such embodiments have extensive applications in clinical diagnostics and clinical studies. Typical clinical samples include, but are not limited to, sputum, blood, blood cells (e.g., white cells), tissue or fine needle biopsy samples, urine, peritoneal fluid, and pleural fluid, or cells therefrom. Biological samples can also include sections of tissues, such as frozen sections or formalin-fixed sections taken for histological purposes. Cell cultures are another typical source of biological samples. Cell cultures used as a source of DNA or RNA can be derived from a clinical sample, or can be supplied from a primary cell culture, a subculture, or a cell line from any organism.

Amplification

The nucleic acid sample can be subjected to amplification prior to hybridization and detection of an allelic marker. Methods for amplification of a nucleic acid are well known in the art. In general, amplification of a nucleic acid sample employs a pair of single-stranded oligonucleotide primers together with an enzyme, e.g., DNA polymerase, which replicates (amplifies) a region of the nucleic acid sample, resulting in multiple copies of the region delimited by the sequences that are complementary to the primers. The pair of primers is chosen so as to amplify a region of the nucleic acid sample containing the polymorphic locus. The size of the region amplified is not critical, but the region must be sufficiently large to include not only the polymorphic locus but also enough sequence on either side of the polymorphic locus to permit highly specific binding of the pair of primers to the chosen region. Strategies for designing and synthesizing primers suitable for amplification of a specific region of a nucleic acid sample are known in the art. As is known in the art, each primer of a pair of amplification primers hybridizes to, and is preferably complementary to, opposite strands of an allele. It is preferred that the primers hybridize to a double stranded nucleic acid in locations which are not more than 2 kb apart, and preferably which are much closer together, such as not more than 1 kb, 0.5 kb, 0.2 kb, 0.1 kb, 0.01 kb or 0.001 kb apart. A suitable DNA polymerase can be used as is known in the art. Thermostable polymerases are particularly convenient for thermal cycling of rounds of primer hybridization, polymerization, and melting. Amplification of single stranded nucleic acids can also be employed.

A preferred amplification method is allele-specific amplification. Okayama et al., *J Lab. Clin. Med.* 114:105–113 (1989). In allele-specific amplification, a nucleotide substitution which is characteristic of a given allele is placed at the 3' end of one of the primers. Only that allele which is complementary to the primer will be amplified; another allele, which contains a different nucleotide substitution and is not complementary to the 3' end of the primer, will not be amplified. The amplification reaction itself can be carried out according to the polymerase chain reaction (PCR) (see *PCR Protocols, A Guide to Methods and Applications*, Innis et al., Academic Press, Inc. N.Y., (1990)) or another suitable amplification method. Other suitable amplification methods include, but are not limited to ligase chain reaction (LCR) (see Wu and Wallace, *Genomics*, 4: 560 (1989); Landegren, et al., *Science*, 241: 1077 (1988); and Barringer, et al., *Gene*, 89: 117 (1990)), transcription amplification (Kwoh, et al., *Proc. Natl. Acad. Sci. USA*, 86: 1173 (1989)), and self-sustained sequence replication (Guatelli, et al., *Proc. Nat. Acad. Sci. USA*, 87: 1874 (1990)).

One of skill in the art will appreciate that whatever amplification method is used, if a quantitative result is desired, care must be taken to use a method that maintains or controls for the relative frequencies of the amplified nucleic acids to achieve quantitative amplification. Methods of quantitative amplification are well known to those of skill in the art. For example, quantitative PCR may involve simultaneously co-amplifying a known quantity of a control sequence using the same primers used to amplify the nucleic acids of interest. This 15 provides an internal standard that can be used to calibrate the PCR reaction. The high density array can then include probes specific to the internal standard for quantification of the amplified nucleic acid. Detailed protocols for quantitative PCR are provided in *PCR Protocols, A Guide to Methods and Applications*, Innis et al., Academic Press, Inc. N.Y., (1990).

After the amplification it may be desirable to remove and/or degrade any excess primers and nucleotides. This can be done by washing and/or enzymatic degradation, using such enzymes as endonuclease I and alkaline phosphatase, for example. Other techniques, such as chromatography, magnetic beads, and avidinor streptavidin-conjugated beads, as are known in the art for accomplishing the removal can also be used. It is not necessary to remove or destroy one of two strands of an amplified DNA product.

Labeling the Extension Primer

The primer extension step of the method provides allele-specificity. The primer is designed to terminate at the position of the polymorphic locus. The primer is hybridized to the denatured amplified double stranded DNA. The primer can be extended by one or more labeled nucleotides using, e.g., a mixture of nucleoside triphosphates and a DNA polymerase. A variation of the primer extension reaction called the single base extension reaction can be used. In single-base extension, dideoxynucleotides are used, which permit only the addition of a single nucleotide to the primer. Any DNA-dependent DNA polymerase can be used. These include, but are not limited to, *E. coli* DNA polymerase I, Klenow fragment of DNA polymerase I, T4 DNA polymerase, T7 DNA polymerase, and *T. aquaticus* DNA polymerase. The extension reaction is preferably performed at the $T_M$ of the primer with the template to enhance product formation.

One configuration for carrying out the primer extension step utilizes two different primers which each hybridize to opposite strands of an amplified double stranded DNA. Each primer terminates at the polymorphic locus. The primer extension reaction may be more robust with one strand as a template than the other. In addition, the information obtained from the second strand should confirm the information obtained from the first strand. The primers can bear the same or different 5' tags.

An alternative method for primer extension involves use of reverse transcriptase and one or two primers which hybridize 3' to the polymorphic locus and terminate at the locus. This method may be desirable in cases where "forward" direction primer extension is less robust than is desirable.

The nucleotides added by the primer extension reaction are labeled. The label can be covalently attached to the nucleoside triphosphates which serve as reactants for the extension reaction. The label can be a fluorescent label (e.g., fluorescein, Texas red, rhodamine, green fluorescent protein, and the like) or other label as defined under "Signal Detection" below.

Hybridizing Nucleic Acids to Arrays of Allele-Specific Probes

"Hybridization" refers to the formation of a bimolecular complex of two different nucleic acids through complementary base pairing. Complementary base pairing occurs through non-covalent bonding, usually hydrogen bonding, of bases that specifically recognize other bases, as in the bonding of complementary bases in double-stranded DNA. In this invention, hybridization is carried out between a 5' tag and at least one probe which has been immobilized on a substrate to form an array.

One of skill in the art will appreciate that an enormous number of array designs are suitable for the practice of this invention. An array will typically include a number of probes that specifically hybridize to the sequences (tags) of interest. It is preferred that an array include one or more control probes. In one embodiment, the array is a high density array. A high density array is an array used to hybridize with a target nucleic acid sample to detect the presence of a large number of allelic markers, preferably more than 10, more preferably more than 100, and most preferably more than 1000 allelic markers.

High density arrays are suitable for quantifying small variations in the frequency of an allelic marker in the presence of a large population of heterogeneous nucleic acids. Such high density arrays can be fabricated either by de novo synthesis on a substrate or by spotting or transporting nucleic acid sequences onto specific locations of a substrate. Both of these methods produce nucleic acids which are immobilized on the array at particular locations. Nucleic acids can be purified and/or isolated from biological materials, such as a bacterial plasmid containing a cloned segment of a sequence of interest. Suitable nucleic acids can also be produced by amplification of templates or by synthesis. As a nonlimiting illustration, polymerase chain reaction, and/or in vitro transcription are suitable nucleic acid amplification methods.

Probe Design

The "probes" used here are specially designed to hybridize to a corresponding "tag". Both the probe and tag sequences are specially chosen, typically artificial oligonucleotide sequences that are unrelated to the rest of the target nucleic acid sequence (the amplified region containing the polymorphism). Furthermore, the probe sequence is chosen so as to avoid or minimize crossreactivity or hybridization with any portion of the target nucleic acid except the tag sequence.

Various types of probes can be included in an array. An array includes "test probes." Test probes can be oligonucleotides that range from about 5 to about 45 or 5 to about 500 nucleotides, more preferably from about 10 to about 40 nucleotides and most preferably from about 15 to about 40 nucleotides in length. In particularly preferred embodiments the probes are 20 to 25 nucleotides in length. In another embodiment, test probes are double or single stranded DNA sequences. DNA sequences can be isolated or cloned from natural sources or amplified from natural sources using natural nucleic acids as templates. However, in situ synthesis of probes on the arrays is preferred. The probes have sequences complementary to particular tag sequences of the amplified DNA product which they are designed to detect. Thus, the test probes are capable of specifically hybridizing to the tag portion of the target nucleic acid they are designed to detect.

The term "perfect match probe" refers to a probe which has a sequence that is perfectly complementary to a particular target sequence. The probe is typically perfectly complementary to a portion (subsequence) of the target sequence. The perfect match probe can be a "test probe," a "normalization control probe," an expression level control probe and the like. A perfect match control or perfect match probe is, however, distinguished from a "mismatch control" or "mismatch probe" or "mismatch control probe."

In addition to test probes that bind the tags of interest, the high density array can contain a number of control probes. The control probes fall into two categories: normalization controls and mismatch controls.

Normnalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency, and other factors that may cause the signal of a perfect hybridization to vary between arrays. In a preferred embodiment, signals (e.g., fluorescence intensity) read from all other probes in the array are divided by the signal (e.g., fluorescence intensity) from the control probes, thereby normalizing the measurements.

Virtually any probe can serve as a normalization control. However, it is recognized that hybridization efficiency varies with base composition and probe length. Preferred normalization probes are selected to reflect the average length of the other probes present in the array; however, they can be selected to cover a range of lengths. The normalization control(s) can also be selected to reflect the (average) base composition of the other probes in the array; however in a preferred embodiment, only one or a few normalization probes are used and they are selected such that they hybridize well (i.e. no secondary structure) and do not match any target-specific probes.

Mismatch controls can also be provided for the probes to the tags or for normalization controls. The terms "mismatch control" or "mismatch probe" or "mismatch control probe" refer to a probe whose sequence is deliberately selected not to be perfectly complementary to a particular tag. Mismatch controls are oligonucleotide probes or other nucleic acid probes identical to their corresponding test or control probes except for the presence of one or more mismatched bases. A mismatched base is a base selected so that it is not complementary to the corresponding base in the tag to which the probe would otherwise specifically hybridize. One or more mismatches are selected such that under appropriate hybridization conditions (e.g. stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a 20 mer, a corresponding mismatch probe will have the identical sequence except for a single base mismatch (e.g., substituting a G, a C, or a T for an A) at any of positions 6 through 14 (the central mismatch).

For each mismatch control in a high-density array there typically exists a corresponding perfect match probe that is perfectly complementary to the same particular tag. The mismatch may comprise one or more bases. While the mismatch(s) may be located anywhere in the mismatch probe, terminal mismatches are less desirable, as a terminal mismatch is less likely to prevent hybridization of the tag. In a particularly preferred embodiment, the mismatch is located at or near the center of the probe such that the mismatch is most likely to destabilize the duplex with the tag under the test hybridization conditions.

Mismatch probes provide a control for non-specific binding or cross-hybridization to a nucleic acid in the sample other than the tag to which the probe is directed. Mismatch probes thus indicate whether or not a hybridization is specific. For example, if the tag is present, the perfect match probes should be consistently brighter than the mismatch probes. The difference in intensity between the perfect match and the mismatch probe ($I_{(PM)}$-$I_{(MM)}$) provides a good measure of the concentration of the hybridized material.

The array can also include sample preparation/amplification control probes. These are probes that are complementary to subsequences of control genes selected because they do not normally occur in the nucleic acids of the particular biological sample being assayed. Suitable sample preparation/amplification control probes include, for example, probes to bacterial genes (e.g., Bio B) where the sample in question is from a eukaryote.

In a preferred embodiment, oligonucleotide probes in the high density array are selected to bind specifically to the tags to which they are directed with minimal non-specific binding or cross-hybridization under the particular hybridization conditions utilized. Because the high density arrays of this invention can contain in excess of 1,000,000 different probes, it is possible to provide every probe of a characteristic length that binds to a particular nucleic acid sequence. Thus, for example, the high density array can contain every possible 20-mer sequence complementary to an IL-2 MRNA. However, there may exist 20-mer subsequences that are not unique to the IL-2 MRNA. Probes directed to these subsequences are expected to cross-hybridize with occurrences of their complementary sequence in other regions of the sample genome. Similarly, other probes simply may not hybridize effectively under the hybridization conditions (e.g., due to secondary structure, or interactions with the substrate or other probes). Thus, in a preferred embodiment, the probes that show such poor specificity or hybridization efficiency are identified and excluded either in the high density array itself (e.g.,during fabrication of the array) or in the post-hybridization data analysis.

Forming High Density Arrays

High density arrays are particularly useful for monitoring the presence of allelic markers. The fabrication and application of high density arrays in gene expression monitoring have been disclosed previously in, for example, WO 97/10365, WO 92/10588, U.S. application Ser. No. 08/772, 376 filed Dec. 23, 1996; Ser. No. 08/529,115 filed on Sep. 15, 1995; Ser. No. 08/168,904 filed Dec. 15, 1993; Ser. No. 07/624,114 filed on Dec. 6, 1990, Ser. No. 07/362,901 filed Jun. 7, 1990, all incorporated herein for all purposes by reference. In some embodiments using high density arrays, high density oligonucleotide arrays are synthesized using methods such as the Very Large Scale Immobilized Polymer Synthesis (VLSIPS) disclosed in U.S. Pat. No. 5,445,934 incorporated herein for all purposes by reference. Each oligonucleotide occupies a known location on a substrate. A nucleic acid target sample is hybridized with a high density array of oligonucleotides and then the amount of target nucleic acids hybridized to each probe in the array is quantified.

Synthesized oligonucleotide arrays are particularly preferred for this invention. Oligonucleotide arrays have numerous advantages over other methods, such as efficiency of production, reduced intra- and inter array variability, increased information content, and high signal-to-noise ratio.

Preferred high density arrays comprise greater than about 100, preferably greater than about 1000, more preferably greater than about 16,000, and most preferably greater than 65,000 or 250,000 or even greater than about 1,000,000 different oligonucleotide probes, preferably in less than 1 $cm^2$ of surface area. The oligonucleotide probes range from about 5 to about 50 or about 500 nucleotides, more preferably from about 10 to about 40 nucleotides, and most preferably from about 15 to about 40 nucleotides in length.

Methods of forming high density arrays of oligonucleotides, peptides and other polymer sequences with a minimal number of synthetic steps are known. The oligonucleotide analogue array can be synthesized on a solid substrate by a variety of methods, including, but not limited to, light-directed chemical coupling and mechanically directed coupling. See Pirrung et al., U.S. Pat. No. 5,143,854 (see also PCT Application No. WO 90/15070) and Fodor et al., PCT Publication Nos. WO 92/10092 and WO 93/09668 and U.S. Ser. No. 07/980,523, which disclose methods of forming vast arrays of peptides, oligonucleotides and other molecules using, for example, light-directed synthesis techniques. See also, Fodor et al., *Science*, 251, 767–77 (1991). These procedures for synthesis of polymer arrays are now referred to as VLSIPS™ procedures. Using the VLSIPS™ approach, one heterogeneous array of polymers is converted, through simultaneous coupling at a number of reaction sites, into a different heterogeneous array. See, U.S. application Ser. Nos. 07/796,243 and 07/980,523.

The development of VLSIPS™ technology as described in the above-noted U.S. Pat. No. 5,143,854 and PCT patent publication Nos. WO 90/15070 and 92/10092, is considered pioneering technology in the fields of combinatorial synthesis and screening of combinatorial libraries. More recently, patent application Ser. No. 08/082,937, filed Jun. 25, 1993, describes methods for making arrays of oligonucleotide probes that can be used to check or determine a partial or complete sequence of a target nucleic acid and to detect the presence of a nucleic acid containing a specific oligonucleotide sequence.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5'-photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences have been synthesized on the solid surface. Combinatorial synthesis of different oligonucleotide analogues at different locations on the array is determined by the pattern of illumination during synthesis and the order of addition of coupling reagents.

In the event that an oligonucleotide analogue with a polyamide backbone is used in the VLSIPS™ procedure, it is generally inappropriate to use phosphoramidite chemistry to perform the synthetic steps, since the monomers do not attach to one another via a phosphate linkage. Instead, peptide synthetic methods are substituted. See, e.g., Pirrung et al. U.S. Pat. No. 5,143,854. Peptide nucleic acids are commercially available from, e.g., Biosearch, Inc. (Bedford, MA) which comprise a polyamide backbone and the bases found in naturally occurring nucleosides. Peptide nucleic acids are capable of binding to nucleic acids with high specificity, and are considered "oligonucleotide analogues" for purposes of this disclosure.

Additional methods which can be used to generate an array of oligonucleotides on a single substrate are described in co-pending Applications Ser. No. 07/980,523, filed Nov. 20, 1992, and 07/796,243, filed Nov. 22, 1991 and in PCT Publication No. WO 93/09668. In the methods disclosed in these applications, reagents are delivered to the substrate by either (1) flowing within a channel defined on predefined regions or (2) "spotting" on predefined regions or (3) through the use of photoresist. However, other approaches, as well as combinations of spotting and flowing, can be employed. In each instance, certain activated regions of the substrate are mechanically separated from other regions when the monomer solutions are delivered to the various reaction sites.

A typical "flow channel" method applied to the compounds and libraries of the present invention can generally be described as follows. Diverse polymer sequences are synthesized at selected regions of a substrate or solid support by forming flow channels on a surface of the substrate through which appropriate reagents flow or in which appropriate reagents are placed. For example, assume a monomer "A" is to be bound to the substrate in a first group of selected regions. If necessary, all or part of the surface of the substrate in all or a part of the selected regions is activated for binding by, for example, flowing appropriate reagents through all or some of the channels, or by washing the entire substrate with appropriate reagents. After placement of a channel block on the surface of the substrate, a reagent having the monomer A flows through or is placed in all or some of the channel(s). The channels provide fluid contact to the first selected regions, thereby binding the monomer A on the substrate directly or indirectly (via a spacer) in the first selected regions.

Thereafter, a monomer "B" is coupled to second selected regions, some of which can be included among the first selected regions. The second selected regions will be in fluid contact with a second flow channel(s) through translation, rotation, or replacement of the channel block on the surface of the substrate; through opening or closing a selected valve; or through deposition of a layer of chemical or photoresist. If necessary, a step is performed for activating at least the second regions. Thereafter, the monomer B is flowed through or placed in the second flow channel(s), binding monomer B at the second selected locations. In this particular example, the resulting sequences bound to the substrate at this stage of processing will be, for example, A, B, and AB. The process is repeated to form a vast array of sequences of desired length at known locations on the substrate.

After the substrate is activated, monomer A can be flowed through some of the channels, monomer B can be flowed through other channels, a monomer C can be flowed through still other channels, etc. In this manner, many or all of the reaction regions are reacted with a monomer before the channel block must be moved or the substrate must be washed and/or reactivated. By making use of many or all of the available reaction regions simultaneously, the number of washing and activation steps can be minimized.

One of skill in the art will recognize that there are alternative methods of forming channels or otherwise protecting a portion of the surface of the substrate. For example, according to some embodiments, a protective coating such as a hydrophilic or hydrophobic coating (depending upon the nature of the solvent) is utilized over portions of the substrate to be protected, sometimes in combination with materials that facilitate wetting by the reactant solution in other regions. In this manner, the flowing solutions are further prevented from passing outside of their designated flow paths.

High density nucleic acid arrays can be fabricated by depositing presynthezied or natural nucleic acids in predetermined positions. Synthesized or natural nucleic acids are deposited on specific locations of a substrate by light directed targeting and oligonucleotide directed targeting. Nucleic acids can also be directed to specific locations in much the same manner as the flow channel methods. For example, a nucleic acid A can be delivered to and coupled with a first group of reaction regions which have been appropriately activated. Thereafter, a nucleic acid B can be delivered to and reacted with a second group of activated reaction regions. Nucleic acids are deposited in selected regions. Another embodiment uses a dispenser that moves from region to region to deposit nucleic acids in specific spots. Typical dispensers include a micropipette or capillary pin to deliver nucleic acid to the substrate and a robotic system to control the position of the micropipette with respect to the substrate. In other embodiments, the dispenser includes a series of tubes, a manifold, an array of pipettes or capillary pins, or the like so that various reagents can be delivered to the reaction regions simultaneously.

Hybridization Conditions

The term "stringent conditions" refers to conditions under which a probe will hybridize to its tag subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH.

The $T_m$ is the temperature, under defined ionic strength, pH, and nucleic acid concentration, at which 50% of the probes complementary to the target sequence hybridize to the target sequence at equilibrium. As the target sequences are generally present in excess, at $T_m$, 50% of the probes are occupied at equilibrium). Typically, stringent conditions will be those in which the salt concentration is at least about 0.01 to 1.0 M concentration of a Na or other salt at pH 7.0 to 8.3 and the temperature is at least about 30° C. for short probes (e.g., 10 to 50 nucleotides). Stringent conditions can also be achieved with the addition of destabilizing agents such as formamide.

The phrase "hybridizing specifically to" refers to the binding, duplexing, or hybridizing of a molecule substantially to or only to a particular nucleotide sequence or sequences under stringent conditions when that sequence is present in a complex mixture (e.g., total cellular) of DNA or RNA. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches.

One of skill in the art will appreciate that hybridization conditions can be selected to provide any degree of stringency. In a preferred embodiment, hybridization is performed at low stringency, in this case in 6×SSPE-T at 37° C. (0.005% Triton X-100), to ensure hybridization, and then subsequent washes are performed at higher stringency (e.g., 1×SSPE-T at 37° C.) to eliminate mismatched hybrid duplexes. Successive washes can be performed at increasingly higher stringency (e.g., down to as low as 0.25× SSPE-T at 37° C. to 50° C.) until a desired level of hybridization specificity is obtained. Stringency can also be increased by addition of agents such as formamide. Hybridization specificity can be evaluated by comparison of hybridization to the test probes with hybridization to the various controls that can be present (e.g., expression level control, normalization control, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. Thus, in a preferred embodiment, the hybridized array can be washed at successively higher stringency solutions and read between each wash. Analysis of the data sets thus produced will reveal a wash stringency above which the hybridization pattern is not appreciably altered and which provides adequate signal for the particular oligonucleotide probes of interest.

The stability of duplexes formed between RNAs or DNAs are generally in the order of RNA:RNA>RNA:DNA>DNA:DNA, in solution. Long probes have better duplex stability with a target, but poorer mismatch discrimination than shorter probes (mismatch discrimination refers to the measured hybridization signal ratio between a perfect match probe and a single base mismatch probe). Shorter probes (e.g., 8-mers) discriminate mismatches very well, but the overall duplex stability is low.

Altering the thermal stability ($T_m$) of the duplex formed between the target and the probe using, e.g., known oligonucleotide analogues allows for optimization of duplex stability and mismatch discrimination. One useful aspect of altering the Tm arises from the fact that adenine-thymine (A-T) duplexes have a lower $T_m$ than guanine-cytosine (G-C) duplexes, due in part to the fact that the A-T duplexes have two hydrogen bonds per base-pair, while the G-C duplexes have three hydrogen bonds per base pair. In heterogeneous oligonucleotide arrays in which there is a non-uniform distribution of bases, it is not generally possible to optimize hybridization for each oligonucleotide probe simultaneously. Thus, in some embodiments, it is desirable to selectively destabilize G-C duplexes and/or to increase the stability of A-T duplexes. This can be accomplished, e.g., by substituting guanine residues in the probes of an array which form G-C duplexes with hypoxanthine, or by substituting adenine residues in probes which form A-T duplexes with 2,6 diaminopurine or by using tetramethyl ammonium chloride (TMACl) in place of NaCl.

Altered duplex stability conferred by using oligonucleotide analogue probes can be ascertained by following, e.g., fluorescence signal intensity of oligonucleotide analogue arrays hybridized with a target oligonucleotide over time. The data allow optimization of specific hybridization conditions at, e.g., room temperature.

Another way of verifying altered duplex stability is by following the signal intensity generated upon hybridization with time. Previous experiments using DNA targets and DNA chips have shown that signal intensity increases with time, and that the more stable duplexes generate higher signal intensities faster than less stable duplexes. The signals reach a plateau or "saturate" after a certain amount of time due to all of the binding sites becoming occupied. These data allow for optimization of hybridization, and determination of the best conditions at a specified temperature.

Methods of optimizing hybridization conditions are well known to those of skill in the art (see, e.g., *Laboratory Techniques in Biochemistry and Molecular Biology*, Vol. 24: *Hybridization With Nucleic Acid Probes*, P. Tijssen, ed. Elsevier, N.Y., (1993)).

Signal Detection

The hybridized nucleic acids can be detected by detecting one or more labels attached to the target nucleic acids. The labels can be incorporated by any of a number of means well known to those of skill in the art. However, in a preferred embodiment, the label is incorporated by labeling the extension primer by carrying out a single base extension reaction using a fluorescently labeled nucleotide.

Detectable labels suitable for use in the present invention include any composition detectable by spectroscopic, photochemical, biochemical, immunochemical, electrical, optical, or chemical means. Useful labels in the present invention include high affinity binding labels such as biotin for staining with labeled streptavidin conjugate, magnetic beads (e.g., Dynabeads™), fluorescent dyes (e.g., fluorescein, Texas red, rhodamine, green fluorescent protein, and the like), radiolabels (e.g., $^3H$, $^{125}I$, $^{35}S$, $^{14}C$, or $^{32}P$), enzymes (e.g., horseradish peroxidase, alkaline phosphatase and others commonly used in an ELISA), epitope labels, and calorimetric labels such as colloidal gold or colored glass or plastic (e.g., polystyrene, polypropylene, latex, etc.) beads. Patents teaching the use of such labels include U.S. Pat. Nos. 3,817,837; 3,850,752;3,939,350;3,996,345;4,277,437;4, 275,149; and 4,366,241.

Means of detecting such labels are well known to those of skill in the art. Thus, for example, radiolabels can be detected using photographic film or scintillation counters, fluorescent markers can be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label. One method uses colloidal gold label that can be detected by measuring scattered light.

The label can be added to the amplification products prior to, or after the hybridization. So called "direct labels" are detectable labels that are directly attached to or incorporated into the tagged nucleic acids prior to hybridization. In contrast, so called "indirect labels" are joined to the hybrid duplex after hybridization. Often, the indirect label is attached to a binding moiety that has been attached to the amplified nucleic acid prior to the hybridization. Thus, for example, the amplified nucleic acid can be biotinylated before the hybridization. After hybridization, an avidin-conjugated fluorophore will bind the biotin-bearing hybrid duplexes, providing a label that is easily detected. For a detailed review of methods of labeling nucleic acids and detecting labeled hybridized nucleic acids see *Laboratory Techniques in Biochemistry and Molecular Biology*, Vol. 24: *Hybridization With Nucleic Acid Probes*, P. Tijssen, ed. Elsevier, N.Y., (1993)).

Means of detecting labeled nucleic acids hybridized to the probes of the array are known to those of skill in the art. Thus, for example, where a calorimetric label is used, simple visualization of the label is sufficient. Where a radioactive labeled probe is used, detection of the radiation (e.g. with photographic film or a solid state detector) is sufficient.

Detection of target nucleic acids which are labeled with a fluorescent label can be accomplished with fluorescence microscopy. The hybridized array can be excited with a light source at the excitation wavelength of the particular fluorescent label and the resulting fluorescence at the emission wavelength is detected. The excitation light source can be a laser appropriate for the excitation of the fluorescent label.

The confocal microscope can be automated with a computer-controlled stage to automatically scan the entire high density array, i.e., to sequentially examine individual probes or adjacent groups of probes in a systematic manner until all probes have been examined. Similarly, the microscope can be equipped with a phototransducer (e.g., a photomultiplier, a solid state array, a CCD camera, etc.) attached to an automated data acquisition system to automatically record the fluorescence signal produced by hybridization to each oligonucleotide probe on the array. Such automated systems are described at length in U.S. Pat. No: 5,143,854, PCT Application 20 92/10092, and copending U.S. application Ser. No. 08/195,889, filed on Feb. 10, 1994. Use of laser illumination in conjunction with automated confocal microscopy for signal detection permits detection at a resolution of better than about 100 $\mu$m, more preferably better than about 50 $\mu$m, and most preferably better than about 25 $\mu$m.

Two different fluorescent labels can be used in order to distinguish two alleles at each polymorphic locus examined. In such a case, the array can be scanned two times. During the first scan, the excitation and emission wavelengths are set as required to detect one of the two fluorescent labels. For the second scan, the excitation and emission wavelengths are set as required to detect the second fluorescent label. When the results from both scans are compared, the genotype identification or allele frequency can be determined.

Quantification and Determination of Genotypes

The term "quantifying" when used in the context of quantifying hybridization of a nucleic acid sequence or subsequence can refer to absolute or to relative quantification. Absolute quantification can be accomplished by inclusion of known concentration(s) of one or more target nucleic acids (e.g., control nucleic acids such as Bio B, or known amounts the target nucleic acids themselves) and referencing the hybridization intensity of unknowns with the known target nucleic acids (e.g., through generation of a standard curve). Alternatively, relative quantification can be accomplished by comparison of hybridization signals between two or more genes, or between two or more treatments to quantify the changes in hybridization intensity and, by implication, the frequency of an allele. Relative quantification can also be used to merely detect the presence or absence of an allele in the target nucleic acids. In one embodiment, for example, the presence or absence of an allelic form of a polymorphic locus can be determined by measuring the quantity of the labeled tag at the known location in the array, i.e., on the solid support, of the corresponding probe.

A preferred quantifying method is to use a confocal microscope and fluorescent labels. The GeneChip® system (Affymetrix, Santa Clara, Calif.) is particularly suitable for quantifying the hybridization; however, it will be apparent to those of skill in the art that any similar system or other effectively equivalent detection method can also be used.

Methods for evaluating the hybridization results vary with the nature of the specific probes used, as well as the controls. Simple quantification of the fluorescence intensity for each probe can be determined. This can be accomplished simply by measuring signal strength at each location (representing a different probe) on the high density array (e.g., where the label is a fluorescent label, detection of the fluorescence intensity produced by a fixed excitation illumination at each location on the array).

One of skill in the art, however, will appreciate that hybridization signals will vary in strength with efficiency of hybridization, the amount of label on the sample nucleic acid and the amount of the particular nucleic acid in the sample. Typically nucleic acids present at very low levels (e.g., <1 pM) will show a very weak signal. At some low level of concentration, the signal becomes virtually indistinguishable from background. In evaluating the hybridization data, a threshold intensity value can be selected below which a signal is counted as being essentially indistinguishable from background.

The terms "background" or "background signal intensity" refer to hybridization signals resulting from non-specific binding, or other interactions, between the labeled target nucleic acids and components of the oligonucleotide array (e.g., the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target allele, for the lowest 5% to 10% of the probes for each allele. However, where the probes to a particular allele hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g., probes directed to nucleic acids of the opposite sense or to genes not found in the sample, such as bacterial genes where the sample is mammalian nucleic acids). Background can also be calculated as the average signal intensity produced by regions of the array that lack any probes at all. In a preferred embodiment, background signal is reduced by the use of a detergent (e.g., C-TAB) or a blocking reagent (e.g., sperm DNA, cot-1 DNA, etc.) during the hybridization to reduce non-specific binding. In a particularly preferred embodiment, the hybridization is performed in the presence of about 0.5 mg/ml DNA (e.g., herring sperm DNA). The use of blocking agents in hybridization is well known to those of skill in the art (see, e.g., Chapter 8 in P. Tijssen, supra).

The high density array can include mismatch controls. In a preferred embodiment, there is a mismatch control having a central mismatch for every probe in the array, except the normalization controls. It is expected that after washing in stringent conditions, where a perfect match would be expected to hybridize to the probe, but not to the mismatch, the signal from the mismatch controls should only reflect non-specific binding or the presence in the sample of a nucleic acid that hybridizes with the mismatch. Where both the probe in question and its corresponding mismatch control show high signals, or the mismatch shows a higher signal than its corresponding test probe, there is a problem with the hybridization and the signal from those probes is ignored. For a given polymorphic locus, the difference in hybridization signal intensity ($I_{allele1}-I_{allele2}$) between an allele-specific probe (perfect match probe) for a first allele and the corresponding probe for a second allele or an average of several other alleles (or other mismatch control probe) is a measure of the presence of or concentration of the first allele. Thus, in a preferred embodiment, the signal of the mismatch probe is subtracted from the signal for its corresponding test probe to provide a measure of the signal due to specific binding of the test probe.

The concentration of a particular sequence can then be determined by measuring the signal intensity of each of the probes that bind specifically to that gene and normalizing to the normalization controls. Where the signal from the probes is greater than the mismatch, the mismatch is subtracted. Where the mismatch intensity is equal to or greater than its corresponding test probe, the signal is ignored (i.e., the signal cannot be evaluated).

For each polymorphic locus analyzed, the genotype can be unambiguously determined by comparing the hybridization patterns obtained to the known locations of the allele-specific probes. When analyzing a DNA sample from a single individual, significant detection of hybridization to a probe indicates the presence of the corresponding allelic form in the genome of the individual. Marginal detection of hybridization, indicated by an intermediate positive result (e.g., less than 1%, or from 1–5%, or from 1–10%, or from 2–10%, or from 5–10%, or from 1–20%, or from 2–20%, or from 5–20%, or from 10–20% of the average of all positive hybridization results obtained for the entire array) may indicate either cross-hybridization or cross-amplification.

Further procedures for data analysis are disclosed in U.S. application Ser. No. 08/772,376, previously incorporated for all purposes.

Determination of Allele Frequency

The "allele frequency" is the frequency with which a selected allelic form of a gene exists within a population or selected group of organisms. Allele frequency is determined from the relative intensity of hybridization to probes. The frequency of a selected allelic form can be quantified as the detected number of copies of the selected allele divided by the total number of alleles of the gene possessed by the individuals tested. Statistical methods are available to determine whether the number of individuals tested is representative of a given population. The ratio of different allelic forms in a population can also be determined using the methods described above. For example, if the DNA sample analyzed contains a mixture of DNA from a population of individuals, then the ratio of different allelic forms in the population is measured directly as the ratio of the relative intensities of the label which hybridizes to the probes corresponding to those allelic forms.

It is understood that the examples and embodiments described herein are for illustrative purposes only and that various modifications or changes will be suggested to persons skilled in the art and are to be included within the spirit and purview of this application and scope of the appended claims. All publications, patents, and patent applications cited herein are hereby incorporated by reference for all purposes.

We claim:

1. A method to aid in detecting a selected allele of a gene in a sample, comprising the steps of:

amplifying a region of DNA in the sample, wherein the region comprises a polymorphic locus of the selected allele of the gene, to form an amplified DNA product;

labeling an extension primer in the presence of the amplified DNA product, wherein the amplified DNA product serves as a template for the step of labeling, wherein the extension primer comprises a 3' portion which is complementary to the amplified DNA product and a 5' portion which is not complementary to the amplified DNA product, wherein the extension primer terminates in a 3' nucleotide at the polymorphic locus of the selected allele, whereby at least one labeled nucleotide is coupled to the 3' terminal nucleotide of the extension primer to form a labeled extension primer; and hybridizing the labeled extension primer to a probe on a solid support, wherein at least a portion of the probe is complementary to the 5' portion of the extension primer.

2. The method of claim 1 additionally comprising the step of:

detecting the label on the solid support, wherein the presence of the label on the solid support indicates the presence of the selected allele in the sample.

3. The method of claim 1 wherein the label is fluorescent.

4. The method of claim 1 wherein the label is radioactive.

5. The method of claim 1 wherein the label is enzymatic.

6. The method of claim 1 wherein the label is epitopic.

7. The method of claim 1 wherein the solid support is beads.

8. The method of claim 1 wherein the solid support is a microtiter dish.

9. The method of claim 1 wherein the DNA is genomic.

10. The method of claim 1 wherein the DNA is cDNA.

11. The method of claim 1 wherein the DNA is mitochondrial.

12. The method of claim 1 wherein the DNA is viral.

13. The method of claim 1 wherein the DNA in the sample was obtained from more than one individual.

14. The method of claim 1 wherein labeled extension products of a plurality of samples from one or more individuals are mixed prior to the step of hybridizing.

15. The method of claim 1 wherein extension primers complementary to two or more selected alleles of the gene are used in the step of labeling.

16. The method of claim 15 wherein quantities of label at known locations on the solid support are compared and a ratio of nucleotides at the polymorphic locus in the sample is determined.

17. The method of claim 16 wherein the sample comprises DNA from two or more individuals.

18. The method of claim 1 wherein primers complementary to selected alleles at two or more polymorphic loci are used in the steps of amplifying and labeling.

19. The method of claim 18 wherein quantities of label at known locations on the solid support are compared and a ratio of nucleotides at each polymorphic locus is determined.

20. The method of claim 19 wherein the sample comprises DNA from two or more individuals.

21. A method to aid in detecting a selected allele of a gene in a sample, comprising the steps of:
   amplifying a region of DNA in the sample, wherein the region comprises a polymorphic locus of the selected allele of the gene using an amplification primer to form an amplified DNA product, wherein the primer terminates in a 3' nucleotide at the polymorphic locus of the selected allele;
   labeling an extension primer in the presence of the amplified DNA product, wherein the amplified DNA product serves as a template for the step of labeling, wherein the extension primer comprises a 3' portion which is complementary to the amplified DNA product and a 5' portion which is not complementary to the amplified DNA product, wherein the extension primer terminates in a 3' nucleotide at the polymorphic locus of the selected allele, whereby at least one labeled nucleotide is coupled to the 3' terminal nucleotide of the extension primer to form a labeled extension primer; and
   hybridizing the labeled extension primer to a probe on a solid support, wherein at least a portion of the probe is complementary to the 5' portion of the extension primer.

22. The method of claim 21 additionally comprising the step of:
   detecting the label on the solid support, wherein the presence of the label on the solid support indicates the presence of the selected allele in the sample.

23. The method of claim 21 wherein the label is fluorescent.

24. The method of claim 21 wherein the label is enzymatic.

25. The method of claim 21 wherein the label is epitopic.

26. The method of claim 21 wherein the label is radioactive.

27. The method of claim 21 wherein the solid support is beads.

28. The method of claim 21 wherein the solid support is a microtiter dish.

29. The method of claim 21 wherein the DNA is genomic.

30. The method of claim 21 wherein the DNA is cDNA.

31. The method of claim 21 wherein the DNA is mitochondrial.

32. The method of claim 21 wherein the DNA is viral.

33. The method of claim 21 wherein the DNA in the sample was obtained from more than one individual.

34. The method of claim 21 wherein labeled extension products of a plurality of samples from more than one individual are mixed prior to the step of hybridizing.

35. The method of claim 21 wherein extension primers complementary to two or more selected alleles of the gene are used in the step of labeling.

36. The method of claim 35 wherein quantities of label at known locations on the solid support are compared and a ratio of nucleotides at the polymorphic locus in the sample is determined.

37. The method of claim 36 wherein the sample comprises DNA from two or more individuals.

38. The method of claim 21, wherein primers complementary to selected alleles at two or more polymorphic loci are used in the steps of amplifying and labeling.

39. The method of claim 38 wherein quantities of label at known locations on the solid support are compared and a ratio of nucleotides at the polymorphic locus in the sample is determined.

40. The method of claim 39 wherein the sample comprises DNA from two or more individuals.

41. A kit comprising in a single container a set of primers for use in detecting a selected allele of a gene, said set comprising:
   a pair of amplification primers which amplify a region of the gene comprising a polymorphic locus; and
   an extension primer, wherein the extension primer terminates in a 3' nucleotide which is at the polymorphic locus of the selected allele, wherein a 3' portion of the extension primer is complementary to the selected allele, wherein a 5' portion of the extension primer is complementary to all or a portion of a probe on a solid support but not complementary to the amplified region of the gene.

42. The kit of claim 41 which comprises two or more extension primers, wherein the 3' portion of each extension primer is complementary to a different allele of the gene.

43. The kit of claim 41 which comprises two or more sets of primers, wherein each amplification primer pair is complementary to a different gene.

44. The kit of claim 41 further comprising one or more solid supports comprising one or more probes, wherein all or a portion of said one or more probes is complementary to the 5' portion of an extension primer.

45. A kit comprising in a single container a set of primers for use in detecting an allele of a gene, said set comprising:
   a pair of amplification primers which specifically amplify a selected allele, wherein the pair of primers comprises a first and a second primer, wherein the first and second primers are complementary to opposite strands of the selected allele, wherein the first primer terminates in a 3' nucleotide which is at a polymorphic locus of the selected allele; and
   an extension primer, wherein a 3' portion of the extension primer is complementary to the selected allele and terminates in a 3' nucleotide which is at the polymorphic locus of the selected allele, wherein a 5' portion of the extension primer is complementary to a probe on a solid support but not complementary to the amplified region of the DNA target.

46. The kit of claim 45 which comprises two or more sets of primers, wherein the first primer of each amplification primer pair is complementary to a different allele.

47. The kit of claim 45 further comprising one or more solid supports comprising one or more probes, wherein all or a portion of the one or more probes is complementary to a 5' portion of an extension primer of a selected allele.

48. A method to aid in detecting a selected allele of a gene in a sample, comprising the steps of:
   labeling an extension primer in the presence of DNA in a sample which comprises a gene, wherein the DNA serves as a template for the step of labeling, wherein the extension primer comprises a 3' portion which is complementary to the DNA and a 5' portion which is not complementary to the DNA, wherein the extension primer terminates in a 3' nucleotide at the polymorphic locus of the selected allele, whereby at least one labeled nucleotide is coupled to the 3' terminal nucleotide of the extension primer to form a labeled extension primer; and hybridizing the labeled extension primer to a probe on a solid support, wherein at least a portion of the probe is complementary to the 5' portion of the extension primer.

49. The method of claim 48 additionally comprising the step of:

detecting the label on the solid support, wherein the presence of the label on the solid support indicates the presence of the selected allele in the sample.

50. The method of claim 48 wherein the label is fluorescent.

51. The method of claim 48 wherein the label is radioactive.

52. The method of claim 48 wherein the label is enzymatic.

53. The method of claim 48 wherein the label is epitopic.

54. The method of claim 48 wherein the DNA in the sample was obtained from more than one individual.

55. The method of claim 48 wherein labeled extension products of samples from more than one individual are mixed prior to the step of hybridizing.

56. The method of claim 48 wherein extension primers complementary to two or more selected alleles of the gene are used in the step of labeling.

57. The method of claim 56 wherein quantities of label at known locations on the solid support are compared and a ratio of nucleotides at the polymorphic locus in the sample is determined.

58. The method of claim 57 wherein the sample comprises DNA from two or more individuals.

59. The method of claim 48 wherein primers complementary to selected alleles at two or more polymorphic loci are used in the step of labeling.

60. The method of claim 59 wherein quantities of label at known locations on the solid support are compared and a ratio of nucleotides at the polymorphic locus in the sample is determined.

61. The method of claim 60 wherein the sample comprises DNA from two or more individuals.

62. The method of claim 48 wherein the solid support is beads.

63. The method of claim 48 wherein the solid support is a microtiter dish.

64. The method of claim 48 wherein the DNA is genomic.

65. The method of claim 48 wherein the DNA is cDNA.

66. The method of claim 48 wherein the DNA is mitochondrial.

67. The method of claim 48 wherein the DNA is viral.

68. The method of claim 1 wherein the solid support is an array.

69. The method of claim 21 wherein the solid support is an array.

70. The kit of claim 44 wherein the one or more solid supports are arrays.

71. The kit of claim 47 wherein the one or more solid supports are arrays.

72. The method of claim 48 wherein the solid support is an array.

* * * * *

UNITED STATES PATENT AND TRADEMARK OFFICE
CERTIFICATE OF CORRECTION

PATENT NO. : 6,287,778 B1 Page 1 of 1
DATED : September 11, 2001
INVENTOR(S) : Xiaohua Huang et al.

It is certified that error appears in the above-identified patent and that said Letters Patent is hereby corrected as shown below:

<u>Column 21,</u>
Line 59, delete "vi ral" and insert -- viral --.

Signed and Sealed this

Twenty-third Day of July, 2002

*Attest:*

*Attesting Officer*

JAMES E. ROGAN
*Director of the United States Patent and Trademark Office*